United States Patent [19]

Blum et al.

[11] Patent Number: 4,962,229

[45] Date of Patent: Oct. 9, 1990

[54] OLEFINIC DIPHOSPHONIC ACIDS, A PROCESS FOR THEIR PRODUCTION, THEIR USE AS THRESHOLDERS, AND COMPLEXING COMPOSITIONS CONTAINING THEM

[75] Inventors: Helmut Blum, Duesseldorf; Siglinde Hemmann, Meerbusch, both of Fed. Rep. of Germany

[73] Assignee: Henkel Kommanditgesellschaft auf Aktien, Duesseldorf, Fed. Rep. of Germany

[21] Appl. No.: 374,323

[22] Filed: Jun. 30, 1989

Related U.S. Application Data

[62] Division of Ser. No. 223,473, Jul. 22, 1988, Pat. No. 4,880,575.

[30] Foreign Application Priority Data

Jul. 25, 1987 [DE] Fed. Rep. of Germany ....... 3724653

[51] Int. Cl.$^5$ .............................................. C07F 9/38
[52] U.S. Cl. ...................... 562/21; 549/78; 549/218; 562/13; 562/22
[58] Field of Search ............... 562/21, 13; 549/78, 549/218

[56] References Cited

U.S. PATENT DOCUMENTS

| | | | |
|---|---|---|---|
| 3,062,792 | 11/1962 | McConnell et al. | 562/21 |
| 3,544,509 | 12/1970 | Carroll et al. | 562/21 |
| 3,576,793 | 4/1971 | Carroll et al. | 562/21 |
| 3,808,237 | 4/1974 | Kerst | 562/21 |

OTHER PUBLICATIONS

Blum, Zeitschrift fur Naturforschung B (Chemical Sciences), Band 43, No. 1, Jan. 1980, pp. 75–81, Tubingen, W. Germany.

*Primary Examiner*—J. E. Evans
*Attorney, Agent, or Firm*—Ernest G. Szoke; Wayne C. Jaeschke; Henry E. Millson, Jr.

[57] ABSTRACT

3-$R^1$-3-oxoprop-1-ene-1,1-diphosphonic acids corresponding to the following general formula

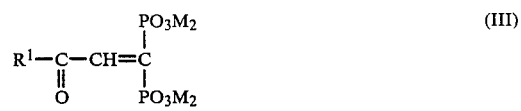

in which
 $R^1$ is a tertiary substituted alkyl group, an optionally substituted cycloalkyl group, or an optionally substituted aryl or heteroaryl group, and
 M is hydrogen or the cation of a base;

to a process for their production in which 3-$R^1$-3-oxo-1-aminopropane-1,1-diphosphonic acids corresponding to the following general formula

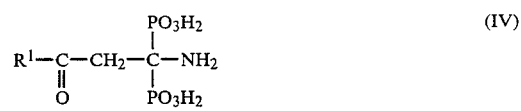

in which $R^1$ is as defined above, are reacted with an aqueous or alcoholic alkali metal hydroxide solution; then water followed by an alcohol infinitely miscible with water is added to the reaction mixture, and the pure olefinic diphosphonic acids are obtained by addition of an acid; to the use of the above compounds of formula III as complexing agents and as thresholders; and to compositions containing one or more compounds of formula (III).

10 Claims, 1 Drawing Sheet

+: COMPOUND OF EXAMPLE 2, TETRASODIUM SALT
✱: COMPOUND OF EXAMPLE 1, TETRASODIUM SALT
⊖: ETHYLENE DIPHOSPHONIC ACID, FOR COMPARISON

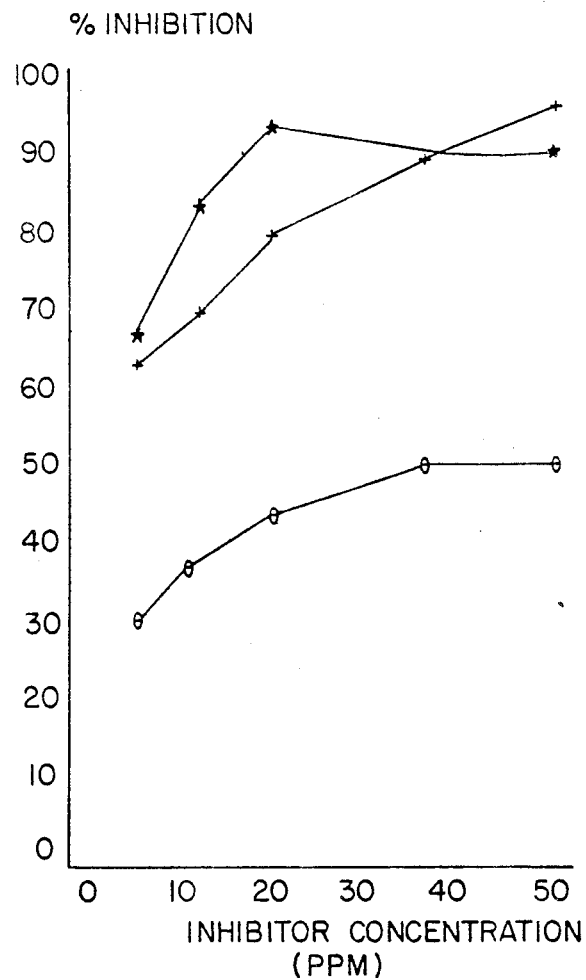
+ : COMPOUND OF EXAMPLE 2, TETRASODIUM SALT
★ : COMPOUND OF EXAMPLE 1, TETRASODIUM SALT
θ : ETHYLENE DIPHOSPHONIC ACID, FOR COMPARISON

OLEFINIC DIPHOSPHONIC ACIDS, A PROCESS FOR THEIR PRODUCTION, THEIR USE AS THRESHOLDERS, AND COMPLEXING COMPOSITIONS CONTAINING THEM

This application is a division, of application Ser. No. 07/223,473, filed 7/22/88, now U.S. Pat. No. 4,880,575.

BACKGROUND OF THE INVENTION

1. Field of the Invention

This invention relates to 3-$R^1$-3-oxoprop-1-ene-1,1-di-phosphonic acids and salts thereof, to a process for their production, to their use as thresholders, and to complexing composition containing them.

2. Statement of Related Art 1-amino-1,1-diphosphonic acids corresponding to the following general formula

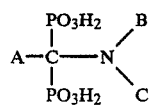  (I)

in which A, B and C represent aliphatic, cycloaliphatic or aromatic hydrocarbon radicals, in addition to which B and C can also represent a hydrogen atom, are known from the prior art. They are prepared by reaction of nitriles with phosphorus trihalides and subsequent hydrolysis or alcoholysis (German application No. 10 02 355), reaction of nitriles with phosphorous acid (German application No. 26 25 767) or reaction of carboxylic acid amides with phosphorus trihalides in the presence of phosphorous acid and subsequent hydrolysis (German application No. 19 58 123). Phosphonic acids corresponding to general formula (I) above have the ability to complex heavy metal ions and alkaline earth metal ions. Accordingly, they are widely used as complexing agents or chelating agents in the softening of water, in detergent manufacture, in the textile field and in paper-making.

It is known from German application No. 16 17 729 that 1-hydroxyethane-1,1-diphosphonic acid can be used as a complexing agent for inhibiting the formation of tartar.

In addition, structurally related compounds corresponding to the following general formula

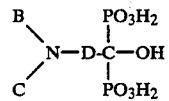  (II)

are known as complexing agents. In formula (II), B and C represent hydrogen or aliphatic or aromatic radicals in analogy to general formula (I) above, while D is a $C_1$-$C_5$ alkylene radical. German application No. 34 34 667 and German patent No. 25 34 391 describe the use of compounds corresponding to general formula (II) and water-soluble salts thereof as complexing agents for alkaline earth metal ions, preferably calcium ions, and as thresholders.

U.S. Pat. No. 2,026,078 describes the synthesis of ethylene-1,1-diphosphonic acid and its use as a complexing agent for heavy metals.

BRIEF DESCRIPTION OF THE DRAWING

The drawing is in chart form showing the threshold effect of the compounds of the invention against calcite scale-formation from synthetic salt water.

DESCRIPTION OF THE INVENTION

Other than in the operating examples, or where otherwise indicated, all numbers expressing quantities of ingredients or reaction conditions used herein are to be understood as modified in all instances by the term "about".

It has now surprisingly been found that new compounds can be obtained by heating 3-$R^1$-3-oxo-1-aminopropane-1,1-diphosphonic acids with aqueous alkali metal hydroxide solutions and that these compounds show favorable complexing properties and are therefore useful as thresholders in compositions for inhibiting calcite scaling. In this particular application, they prevent the deposition of calcite, even at very high scale-forming concentrations, such as occur for example in oil recovery when formation water and sea water encounter one another.

The formation of the olefinic diphosphonic acids of the invention was unexpected because 1-aminoalkane-1,1-diphosphonic acids are supposed to be stable to alkali metal hydroxides, even on boiling. In fact, a rearrangement to 1,2-diphosphonic acids corresponding to the following formula

might rather have been expected to occur, as known for the corresponding analogous compounds $ClCH_2(NH_2)(PO_3H_2)_2$ from M. Fukuda et al. Chem. Lett. 1977, 1079 and K. H. Worms, H. Blum and H. U. Hempel, Z. anorg. allg. Chem. 457 (1979), 214.

The present invention relates to 3-$R^1$-3-oxoprop-1-ene-1,1-diphosphonic acids corresponding to the following general formula

  (III)

in which $R^1$ represents
 a tertiary alkyl group having the general formula
  —$(R^2)C(R^3)(R^4)$, where $R^2$ and $R^3$ independently of one another represent a $C_1$-$C_3$ alkyl group while $R^4$ represents a $C_1$-$C_{10}$ alkyl group,
 an optionally substituted cycloalkyl group, or
 an aryl or heteroaryl group optionally substituted by halogen, $C_1$-$C_5$ alkoxy, di-$C_1$-$C_5$-alkylamino, or $C_1$-$C_5$ alkyl, and
M is H or the cation of a base,
and the salts thereof.

The present invention also relates to a process for the production of compounds of formula (III) wherein a 3-$R^1$-3-oxo-1-aminopropane-1,1-diphosphonic acid corresponding to the following general formula

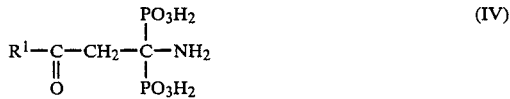  (IV)

in which $R^1$ is as defined above, is reacted with an aqueous or alcoholic alkali metal hydroxide solution at a temperature in the range of 80° to 150° C.; the molar ratio of alkali metal hydroxide to the compound of formula IV being from 5:1 to 20:1. An excess of water is then added to the reaction mixture and the resulting alkali metal salt of the compound of formula (III) is prepcipitated by addition of an alcohol infinitely miscible with water, and optionally dissolved and reprecipitated. The reaction products of formula (III), in which M represents hydrogen, can be isolated therefrom using an acidic reagent. The reaction products of formula (III), in which M represents hydrogen, can then optionally be converted by addition of basic reagents corresponding to the formula $M^+OH^-$, where $M^+$ is an alkali metal or ammonium cation $R^5R^6R^7R^8N^+$, in which $R^5$, $R^6$, $R^7$ and $R^8$ independently of one another can be hydrogen or a branched or unbranched $C_1$–$C_{12}$ alkyl radical, into compounds of formula (III) in which M is an alkali metal or ammonium cation as defined above. The resulting compounds of formula (III) are isolated and purified by methods known per se.

The present invention also relates to the use of the compounds of formula (III) as complexing agents and as thresholders.

The invention also relates to compositions containing one or more compounds corresponding to general formula (III), in which $R^1$, $R^2$, $R^3$, $R^4$ and M are as defined above, in complexing concentrations.

The new compounds of general formula (III) can be called 3-$R^1$-3-oxopro-1-ene-1,1-diphosphonic acids or salts thereof, depending on the substituents $R^1$, $R^2$, $R^3$, $R^4$ and M.

As described above, $R^1$ can be a tertiary alkyl group corresponding to the general formula —$(R^2)C(R^3)(R^4)$. The radicals $R^2$ and $R^3$ independently of one another can be methyl, ethyl, or a propyl group. $R^2$ and $R^3$ are preferably identical. Compounds of formula (III) in which both radicals $R^2$ and $R^3$ are methyl or ethyl are particularly preferred. $R^4$ can be an unbranched or branched $C_1$–$C_{10}$ alkyl radical. Alkyl radicals such as these include methyl, ethyl, n-propyl, i-propyl, n-butyl, sec.-butyl, tert.-butyl, n-pentyl, n-hexyl, n-heptyl, n-octyl, n-nonyl, and n-decyl and also branched isomers thereof. $R^4$ is preferably an unbranched $C_3$–$C_6$ alkyl radical.

$R^1$ can also be an optionally methyl or ethyl substituted $C_3$–$C_6$ cycloalkyl group. If a methyl or ethyl substituent is present, it is preferably present in the 1-position of the cycloalkyl group. Cycloalkyl groups include cyclopropyl, cyclobutyl, cyclopentyl, cyclohexyl, 1-methyl cyclopropyl, 1-methyl cyclobutyl, 1-methyl cyclopentyl and 1-methyl cyclohexyl.

$R^1$ can also be an aryl or heteroaryl group, optionally substituted by halogen, $C_1$–$C_5$ alkoxy, di-$C_1$–$C_5$-alkylamino or $C_1$–$C_5$ alkyl. A particularly suitable aryl group is phenyl. Suitable heteroaryl groups are those which have 5 or 6 members and preferably contain an O, S, or N atom. They can be anellated or condensed. Other optionally substituted aryl or heteroaryl groups include 2-methylphenyl, 3-methylphenyl, 4-methylphenyl, 2,4-dimethylphenyl, 2-fluorophenyl, 3-fluorophenyl, 4-fluorophenyl, 2-chlorophenyl, 3-chlorophenyl, 4-chlorophenyl, 2,4-dichlorophenyl, 3,4-dichlorophenyl, 3,5-dichlorophenyl, 2-methoxyphenyl, 3-methoxyphenyl, 4-methoxyphenyl, 3,4-dimethoxyphenyl, 3,4,5-trimethoxyphenyl, 2-furyl, 3-furyl, 5-bromo-2-methyl-3-furyl, 2-thienyl, 3-thienyl, and 5-methyl-2-thienyl.

Compounds corresponding to formula (III) above in which M—instead of the proton for the free acid-represents an alkali metal cation or an ammonium cation having the general formula $R^5R^6R^7R^8N^+$, have a complexing effect and, accordingly, are preferred in the practice of the invention. A major advantage of these salts derived from the free acid is that they clearly improve the solubility in water of the compounds of formula (III) in which M represents H. The usefulness of such compounds in preparations having a threshold effect is thus also improved. According to the invention, such cations as $Na^+$ or $K^+$ are particularly suitable alkali metal cations. However, M can also represent ammonium cations corresponding to the above general formula, in which $R^5$, $R^6$, $R^7$ and $R^8$ independently of one another can be hydrogen or branched or unbranched $C_1$–$C_{12}$ alkyl radicals. Accordingly, such alkyl radicals are any branched and unbranched radicals including methyl, ethyl, propyl, butyl, pentyl, hexyl, heptyl, octyl, nonyl, decyl, undecyl, and dodecyl. Partial salts in which one to three M groups are hydrogen and the remaining M groups are alkali metal or ammonium cations are also within the scope of the invention.

According to the invention, preferred water-soluble salts are alkali metal salts corresponding to formula (III) in which M represents an alkali metal cation. The sodium salts are particularly preferred.

Although the compounds corresponding to formula (III) are prepared by a process which eliminates ammonia, this process must nevertheless be regarded as chemically unique because an amino group at an α-carbon atom cannot readily be eliminated in a basic medium. According to the invention, this is accomplished by reaction of a 3-$R^1$-3-oxo-1-aminopropane-1,1-diphosphonic acid of formula (IV) with aqueous or alcoholic alkali metal hydroxide solution, the molar ratio of alkali hydroxide to starting material being between 5:1 and 20:1, preferably 12:1. NaOH in aqueous solution is advantageously used as the alkali metal hydroxide for the process of the invention. The production of the 3-$R^1$-3-oxo-1-aminopropane-1,1-diphosphonic acids of the formula (IV), in which $R^1$ is a substituted tertiary alkyl group, used as a starting material is described in published German application No. 36 11 522. Compounds corresponding to formula (IV) in which $R^1$ is an optionally substituted cycloalkyl group or an optionally substituted aryl group or heteroaryl group, can be prepared analogously to this process using the 3-$R^1$-3-oxopropionic acid nitriles known from European patent No. 0 089 011.

The reaction temperatures are in the range of from 80° to 150° C., and preferably in the range of from 100° to 140° C. In practice, the compound of formula (IV) is generally introduced first and the aqueous alkali metal hydroxide subsequently added thereto. The reaction mixture is then stirred for a period of time e.g. 20 to 50 hours at a temperature in the above range until the reaction is complete. The completion of the reaction can be verified by standard chromatographic methods.

The concentration of the alkali metal hydroxide in water or alcohol is from 15 to 50% by weight, preferably from 20 to 25% by weight.

An excess of water is then added to the reaction mixture and the resulting alkali metal salt of the compound of formula (III) is precipitated by addition of an alcohol infinitely miscible with water, and is optionally dissolved and reprecipitated. The reaction product corresponding to formula (II) in which M represents hydrogen, can then be isolated therefrom in known manner using an acid reagent. Alcohols infinitely miscible with water include methanol, ethanol, n-propanol, i-propanol and t-butanol. Methanol is preferred.

Acidic reagents for use herein include the mineral acids, such as hydrochloric acid, sulfuric acid, nitric acid, or phosphoric acid, organic acids, and acidic and strongly acidic ion exchange resins. Strongly acidic ion exchange resins are preferred.

The resulting reaction products corresponding to formula (III) in which M represents hydrogen, are then optionally converted by addition of basic reagents corresponding to the formula $M^+OH^-$, where $M^+$ is an alkali metal or ammonium cation, into their water-soluble salts, preferably their alkali metal salts and more preferably their sodium salts, and are isolated from the reaction mixture and purified by methods known per se. This can be done, for example, by crystallizing out the reaction products dissolved in the reaction mixture at elevated temperature by cooling, or by precipitating the reaction products by addition of a solvent, e.g. an alcohol which is infinitely miscible with water, separating the deposits or crystals obtained from the dissolved reactants either by decanting off the mother liquor or by filtration, subsequently drying the deposits or crystals, and optionally further purifying them by recrystallization.

In addition, it has surprisingly been found that the compounds of formula (III) show excellent complexing properties with respect to alkaline earth ions, particularly calcium ions.

Besides their excellent complexing power, compounds of formula (III) are distinguished by strong threshold activity, i.e. they are capable of preventing the precipitation of poorly soluble alkaline earth metal salts, even in seeding quantities, i.e. substoichiometric quantities.

They can be widely used as complexing agents. For example, they can be used for processes involved in the softening of water, in which case the threshold effect discussed above plays a particular role. Accordingly, there is no need to use stochiometric quantities. Calcite precipitation can be significantly retarded even with substoichiometric quantities.

They are also eminently suitable for use as corrosion and scale inhibitors for cooling waters, particularly in combination with known additives.

To this end, one or more compounds of formula (III), in which $R^1$ is as defined above, is used in a quantity of from 1 to 50 mg/l in compositions used as thresholders against calcite formation. Compositions containing one or more compounds of formula (III) in which $R^1$ is a tertiary alkyl group of the general formula —$(R^2)C(R^3)(R^4)$, $R^4$ is a linear or branched $C_3$–$C_6$ alkyl radical, $R^2$ and $R^3$ represent methyl or ethyl and M is an alkali metal cation, preferably a sodium ion, in concentrations of 5 to 50 mg/l have been found to be particularly effective in this regard.

Compositions such as these are particularly suitable for preventing the deposition of calcite, even at very high scale-forming concentrations. They need only be used in a comparatively low concentration for this purpose, which makes them distinctly superior to other structurally comparable complexing compositions.

The compounds of formula (III) are also suitable for pharmaceutical purposes, for example for the treatment of animal disorders, e.g. human disorders affecting calcium or phosphate metabolism and their associated illnesses. In addition, the compounds of the invention can be used in cosmetic preparations for oral hygiene, such as for example mouthwashes, tooth powders, tooth creams, or toothpastes; in dental fixatives, for the treatment of tartar, and for the prophylaxis of tartar. The compounds of the invention can also be used in conjunction with technetium-99 m for skeletal scintigraphy.

The invention is illustrated but not limited by the following Examples.

EXAMPLES

EXAMPLE 1

0.38 mol 4-ethyl-4-methyl-3-oxo-1-aminohexane-1,1-diphosphonic acid (IV, $R^2=R^3=CH_2CH_3$, $R^4=CH_3$) and 750 ml (4.68 mol) 25% sodium hydroxide were heated for 48 hrs. at 120° C. in a Teflon flask. The reaction product was then taken up in such a quantity of water that a clear solution was formed.

The tetrasodium salt of the 4-ethyl-4-methyl-3-oxohex-1-ene-1,1-diphosphonic acid (III, $R^2=R^3=CH_2CH_3$, $R_4=CH_3$, M=Na) was precipitated by addition of methanol and dissolved and reprecipitated for further purification. The tetrasodium salt was dried in air and was then present as a water-containing product. Yield, 75% of the theoretical. Atomic ratio P:C:Na=2.00:9.16:3.93 (calculated 2:9:4).

To prepare the free acid, a 10% by weight solution of this tetrasodium salt was passed through a column filled with a strongly acidic ion exchange resin. The eluate was then concentrated to an oily consistency and the 4-ethyl-4-methyl-3-oxohex-1-ene-1,1-diphosphonic acid was obtained in the form of anhydrous crystals. Melting point: 146°–147° C.

Elemental analysis (%): Calculated: C 36.00 H 6.00 P 20.66; Found: C 36.10 H 5.93 P 20.60.

EXAMPLE 2

0.38 mol 4,4-dimethyl-3-oxo-1-aminoheptane-1,1-diphosphonic acid (IV, $R^2=R^3=CH_3$, $R^4=n-C_3H_7$) was heated with sodium hydroxide using the same method described in Example 1. The reaction mixture was taken up in water and then worked up in the same way as in Example 1. The yield of 4,4-dimethyl-3-oxohept-1-ene-1,1-diphosphonic acid (III), $R^2=R^3=CH_3$; $R^4=n-C_3H_7$) comprised 73% of the theoretical. Atomic ratio P:C:Na=2.00:8.90:3.89 (calculated 2:9:4).

The free acid was prepared therefrom under the conditions described in Example 1. Melting point: 162° to 163° C.

Elemental analysis (%): Calculated: C 36.00 H 6.00 P 20.66; Found: C 36.14 H 5.89 P 20.60.

EXAMPLE 3

0.38 mol 4,4-dimethyl-3-oxo-1-aminodecane-1,1-diphosphonic acid (IV, $R^2=R^3=CH_3$, $R^4=n-C_6H_{13}$) was converted into the tetrasodium salt of 4,4-dimethyl-3-oxodec-1-ene-1,1-diphosphonic acid (III, $R^2=R^3=-CH_3$, $R^4=n-C_6H_{13}$ M=Na) by the method described in Example 1. The yield was 65% of the theoretical. Atomic ratio P:C:Na=2.00:11.88:4.06 (calculated 2:12:4).

The free acid was prepared under the conditions described in Example 1 and accumulates in paste-like form.

EXAMPLE 4

The threshold activity, i.e. the ability of the complexing agent to prevent or retard the scaling of poorly soluble calcium salts (for example calcite) in substoichiometric quantities, was tested in synthetic saltwaters which correspond in their composition to reservoir injection waters of low salinity.

The threshold activity of the olefinic diphosphonic acids according to the invention was tested with respect to calcite at 5 to 50 ppm.

The calcite scale-forming concentration was 4.133 g calcium carbonate/l and the electrolyte concentration 36 g sodium chloride/l.

The test solutions were stored in a water bath for 3 days at 70° C. and at a pH of 7.3. The amount of calcium salt remaining in solution was then determined.

The determination was carried out by standard test method 03-74 of the National Association of Corrosion Engineers.

The threshold effect of the olefinic diphosphonic acids of the invention is shown in the drawing (Figure).

The threshold activity of ethylene diphosphonic acid was determined for comparison. The results are shown in the Figure which shows the degree of inhibition (in %) as a function of the inhibitor concentration (in ppm).

The symbols used apply to the following compounds:
+: compound of Example 2 as the tetrasodium salt
*: compound of Example 1 as the tetrasodium salt
θ: ethylene diphosphonic acid for comparison.

The comparison of the olefinic diphosphonic acids of Examples 1 and 2 according to the invention in the form of their tetrasodium salts with the known ethylene diphosphonic acid shows that the compounds according to the invention possess considerable complexing power and have a considerably increased threshold effect, reaching an inhibition level of 90% even in low inhibitor concentrations.

We claim:

1. A 3-$R^1$-3-oxoprop-1-ene-1,1-diphosphonic acid corresponding to the formula

wherein $R^1$ represents
a tertiary alkyl group having the formula —$(R^2)C(R^3)(R^4)$, where $R^2$ and $R^3$ independently of one another represent a $C_1$-$C_3$ alkyl group, and $R^4$ represents a $C_1$-$C_{10}$ alkyl group, or an unsubstituted or methyl or ethyl substituted cycloalkyl group, or an aryl or heteroaryl group which is unsubstituted or substituted by halogen, $C_1$-$C_5$ alkoxy, di-$C_1$-$C_5$-alkylamino, or $C_1$-$C_5$ alkyl; and each M group is H or the cation of a base.

2. The compound of claim 1 wherein $R^1$ is a tertiary alkyl group of the formula —$(R^2)C(R^3)(R^4)$ in which $R^4$ is an unbranched $C_3$-$C_6$ alkyl radical and M is a cation of a water-soluble base.

3. The compound of claim 2 wherein $R^2$ and $R^3$ are the same and are either methyl or ethyl.

4. The compound of claim 1 wherein the M groups are all alkali metal cations.

5. The compound of claim 4 wherein the alkali metal cations are sodium ions.

6. The compound of claim 1 wherein the M groups are all ammonium cations of the formula $R^5R^6R^7R^8N^+$ in which $R^5$, $R^6$, $R^7$ and $R^8$ independently of one another are hydrogen or an unbranched or branched $C_1$-$C_{12}$ alkyl radical.

7. The compound of claim 1 wherein $R^1$ is an unsubstituted or methyl or ethyl substituted $C_3$-$C_6$ cycloalkyl group.

8. The compound of claim 1 wherein $R^1$ is a $C_3$-$C_6$ cycloalkyl group substituted in the 1-position with a methyl or ethyl group.

9. The compound of claim 1 wherein $R^1$ is phenyl.

10. The compound of claim 1 wherein $R^1$ is a 5 or 6 membered heteroaryl group containing an O, S, or N atom.

* * * * *